United States Patent [19]
Menon et al.

[11] Patent Number: 5,560,927
[45] Date of Patent: Oct. 1, 1996

[54] CO-PROCESSING METHOD FOR MAKING A FREE-FLOWING COMPRESSIBLE POWDER AND TABLET THEREFROM

[75] Inventors: Anil Menon, West Caldwell; Timothy Gillece, Pompton Plains; Sibu Chakrabarti, Randolph, all of N.J.

[73] Assignee: ISP Investments Inc., Wilmington, Del.

[21] Appl. No.: 508,361

[22] Filed: Jul. 28, 1995

[51] Int. Cl.$^6$ .............................. A61K 9/20; B01J 13/04
[52] U.S. Cl. ............................................. 424/464; 264/4.1
[58] Field of Search ............................... 264/4.1; 424/464

[56] References Cited

U.S. PATENT DOCUMENTS 4,837,031  6/1989  Denton ..................................... 424/264

OTHER PUBLICATIONS

Patel et al., CA Ab. # 111: 140400 CA, 1989.

*Primary Examiner*—Nathan M. Nutter
*Attorney, Agent, or Firm*—Walter Katz; Marilyn J. Maue; Joshua J. Ward

[57] ABSTRACT

A process for making a free-flowing, compressible powder by spraying a selected amount of an aqueous solution of polyvinylpyrrolidone onto a fluid bed containing a predetermined admixture of starch and polyvinylpyrrolidone therein, and drying. An active-containing tablet then is provided by adding an active material, optionally with a lubricant, to such powder, and compressing the admixture into a commercially acceptable tablet.

3 Claims, No Drawings

CO-PROCESSING METHOD FOR MAKING A FREE-FLOWING COMPRESSIBLE POWDER AND TABLET THEREFROM

BACKGROUND OF THE INVENTION

1. Field of the Invention

This invention relates to a process for making free-flowing, compressible powders, and to tableting of an active ingredient therein from such powders, and more particularly, to a co-processing method for forming powders and tablets having advantageous physical and use properties.

2. Description of the Prior Art

Direct compression is a process by which a powder blend of an active ingredient, such as a drug, and a suitable excipient or filler, which is capable of flowing uniformly into a die cavity, are compressed directly into an acceptable tablet. Direct compression excipients or fillers include microcrystalline cellulose, anhydrous lactose, spray dried lactose and dicalcium phosphate.

The advantages of direct compression include avoiding exposure of the active material to moisture and heat, and long-term physical and chemical stability due to the substantial absence of moisture or direct exposure of the drug particles.

The disadvantages of direct compression include the requirement of flowability of the powder blends, especially in high speed tabletting, limited particle bonding and dilution capacities of the filler/binder.

Flowability of the powder blends can be partially overcome by admixture with lubricants; however, this may hinder the hardness of the tablet and dissolution of the drug. Particle bonding and dilution can be overcome by including one or more filler/binders in the tablet. Blending problems also may be overcome by using a filler with a range of particle sizes and/or densities corresponding to the active material.

Co-processing which is defined as the use of a combination of two or more filler/binder materials, for direct compression of tablets, can improve upon the currently available individual excipients without changing their chemical structure.

Starch (Cornstarch USP) is a widely accepted material for pharmaceutical use. Starch is a well known disintegrant in solid dosage form, and its aqueous solutions are advantageous as a binder in wet granulation tableting processes. However, cornstarch alone does not possess two properties necessary for making good compacts, namely compressibility and fluidity. Cornstarch does not form hard compacts under moderate compression forces, and, also, it exhibits only minimal dilution potential. Starch 1500 is the commercially available form of modified starch.

Accordingly, it is an object of this invention to provide an improved co-processing process for making free-flowing, compressible powders, which in combination with an active medicinal material, may be directly compressed to form a tablet having commercially-acceptable fluidity, compressibility, dissolution times, lubricity, and dilution potential.

SUMMARY OF THE INVENTION

A process for making a free-flowing, compressible powder by spraying a selected amount of an aqueous solution of PVP onto a fluid bed containing a predetermined admixture of starch and PVP therein, and drying. An active-containing tablet then is provided by adding an active material, optionally with a lubricant, to such powder, and compressing the admixture into a commercially acceptable tablet.

DETAILED DESCRIPTION OF THE INVENTION

In accordance with the invention, there is provided a co-processing method for making a free-flowing, compressible powder which comprises (a) providing a fluid bed with an admixture of starch and PVP therein, (b) applying an aqueous solution of PVP onto said fluidized admixture, and (c) drying the resultant product.

Thereafter, an active material, such as a medicinal agent, or drug, optionally with a lubricant, is added to the free-flowing, compressible powder obtained by the co-processing process described above, and the admixture is directly compressed into a tablet.

The co-processing process is carried out by first providing a suitable fluid bed with a mixture of about 10–50% of the total PVP content in the final powder product, and starch, in a suitable amount to provide a predetermined amount in the powder.

Then an aqueous PVP solution is sprayed onto the fluid bed to provide an additional 50–90% of the total PVP content in the powder product.

Finally, the product is dried to an 8–15% moisture content to provide a free-flowing, compressible powder having an average particle size of about 100μ to 250μ.

Suitable powders contain about 90% to 99% by weight cornstarch and about 1% to 10% PVP.

The active-containing tablet obtained herein suitably has a compression force of $\leq 2000$ kg, a hardness of $\geq 8$ kp, a dissolution rate $t_{50\%}$ of under 10 minutes, and a $t_{100\%}$ of under 30 minutes. Preferably drying is carried out by continuous fluidization to a moisture content of about 8–15%.

In a typical run, co-processing is carried out using a Uniglatt top-spray fluid bed maintained at about 50°–60° C. and distilled water as the solvent. The bed contained a mixture of 480 g of cornstarch and 10 g of polyvinylpyrrolidone (PVP K 90). Then an additional 10 g of PVP in 220 ml of water is sprayed onto the fluid bed. The resultant product then is dried to a predetermined moisture content.

The binder therein was found to be distributed equally both intragranularly and extragranularly with the free-flowing, compressible powder. The powder then was mixed with a drug and lubricant and compacted at various compressed forces.

The physical properties of the powder of the invention, and tablets with an active therein, are shown in Tables 1 and 2 below.

TABLE 1

| | Properties of Powder of Invention | | | | |
|---|---|---|---|---|---|
| | Applied | Comparative Runs* | | Invention Method** | |
| Ex. No. | Compression Force (kg) | Hardness (kp) | Disintegration Time (min) | Hardness (kp) | Disintegration Time (min) |
| 1 | 1000 | 2.80 | 22.44 | 4.83 | 8.42 |
| 2 | 2000 | 6.13 | 20.89 | 10.22 | 9.01 |
| 3 | 3000 | 10.07 | 23.07 | 13.08 | 7.79 |
| 4 | 4000 | 8.20 | 21.89 | 14.02 | 9.12 |

*All PVP applied onto fluid bed by solution spraying only
**PVP distributed between load on fluid bed and applied by solution spraying

TABLE 2

| | Physical Properties of Drug-Containing Tablets of Invention | | | | | | | |
|---|---|---|---|---|---|---|---|---|
| | Comparative Run* | | | | Invention Method | | | |
| Ex. No. | Applied Compression Force (kg) | Hardness (kp) | Disintegration Time (min) | $Q_{12}$*** (%) | Applied Compression Force (kg) | Hardness (kp) | Disintegration Time (min) | $Q_{12}$ (%) |
| 1 | 4894 | 7.83 | 1.79 | 69.0 | 2918 | 6.48 | 1.34 | 63.0 |

***Percent Drug released at 12 min.

What is claimed is:

1. A co-processing method for making a free-flowing, compressible powder of 90–99% starch and 1–10% polyvinylpyrrolidone, on a dry basis, which comprises
   (a) providing a fluid bed with an admixture of starch and polyvinylpyrrolidone therein,
   (b) applying an aqueous solution containing additional polyvinylpyrrolidone onto said fluidized admixture, wherein about 10–50% of the polyvinylpyrrolidone content in the powder is present in the fluid admixture on a dry weight basis, and about 50–90% of the polyvinylpyrrolidone content in the powder is present in the aqueous solution, and
   (c) drying the resultant product.

2. A method of making an active-containing tablet which comprises the steps of
   (d) adding an active material, optionally with a lubricant, to the free-flowing, compressible powder obtained by the process of claim 1, and
   (e) compressing said admixture directly into a tablet.

3. A process according to claim 1 wherein drying is carried out by continuous fluidization to a moisture content of about 8–15%.

* * * * *